(12) United States Patent
Conti

(10) Patent No.: US 10,898,370 B2
(45) Date of Patent: Jan. 26, 2021

(54) EYELID CLEANING TOOL

(71) Applicant: Thomas Conti, Schererville, IN (US)

(72) Inventor: Thomas Conti, Schererville, IN (US)

(73) Assignee: Thomas Conti, Schererville, IN (US)

( * ) Notice: Subject to any disclaimer, the term of this patent is extended or adjusted under 35 U.S.C. 154(b) by 162 days.

(21) Appl. No.: 15/985,012

(22) Filed: May 21, 2018

(65) Prior Publication Data

US 2019/0350753 A1    Nov. 21, 2019

(51) Int. Cl.
*A61F 9/00*    (2006.01)

(52) U.S. Cl.
CPC ........ *A61F 9/00* (2013.01); *A61F 2250/0093* (2013.01)

(58) Field of Classification Search
CPC .. A61F 9/00; A61F 2250/0093; A61F 9/0008; A46B 2200/1053; A46B 9/02; A46B 13/023; A45D 2200/207; A61H 2205/024
See application file for complete search history.

(56) References Cited

U.S. PATENT DOCUMENTS

| 2010/0300475 | A1 | 12/2010 | Gueret |
| 2012/0065556 | A1 | 3/2012 | Smith et al. |
| 2013/0331768 | A1 | 12/2013 | Nichamin |
| 2015/0182415 | A1 | 7/2015 | Olkowski et al. |
| 2018/0325729 | A1* | 11/2018 | Rynerson ............ A61F 9/00709 |

FOREIGN PATENT DOCUMENTS

WO    2017/066620 A1    4/2017

* cited by examiner

*Primary Examiner* — George J Ulsh
(74) *Attorney, Agent, or Firm* — John S. Paniaguas; Clark Hill PLC

(57) ABSTRACT

A hand-held device for home use is disclosed for cleaning eyelids, eye margins and eye lashes. The device includes a housing, which forms a handle, and a cleaning head, attached on one end. In accordance with an important aspect of the invention, a vibration generator is used to drive the cleaning head sonically. The sonically driven cleaning head is placed in contact with one or both eye lids for each eye and either held in a stationary position or moved from side to side or back and forth. The vibration of the cleaning head in contact with the soap and effectively scrubs the upper eyelid or lower eyelid without the need for vigorous scrubbing or significant agility. The vibrating cleaning head is a more effective daily home cleaning tool for eyelids and eyelashes than known devices with rotary swabs or sponges.

16 Claims, 4 Drawing Sheets

EYELID CLEANING TOOL

BACKGROUND OF THE INVENTION

1. Field of the Invention

The present invention relates to hand held tool for home use for treating various ocular disorders associated with human eyelids.

2. Description of the Prior Art

In order to maintain optimal vision, the human eye requires proper maintenance of all its anatomical structures. A human eye is illustrated in FIGS. 2 and 3. The eyeball 10 (FIG. 2) is protected by a set of movable upper 12 and lower 14 eyelids. The eyelids 12 and 14 function to open and close to protect the eye 10 from dust, debris, wind and excessive light. The anatomy of each eyelid 12 and 14 is very complex and includes structures, such as skin, muscle, fat, lashes and oil glands. Each eyelid 12 and 14 includes eyelashes 16 and 18. The area of the eyelid 12 and 14 around the eyelashes 16 and 18, i.e. the area when the eyelids 12 and 14 close and touch each other, is known as the eyelid margin 20 and 22.

The eyelashes 16 and 18 serve to heighten the protection of the eye from dust and foreign debris, as well as from perspiration. The eyelid margin 20 and 22 and eyelashes 16 and 18 have a unique bacterial flora that needs to be cared for daily fashion to prevent their natural bacteria from over growing and causing various eyelid disorders, such as blepharitis, sties, chalaza. The bacteria is known to result in itching, burning, red, irritated and dry eyes.

The eyelid margin 20 and 22 is also very important to maintain the health of the tear film because it contains special oil glands known as Meibomian glands. These unique eyelid glands supply a thin layer of oil that, upon blinking, floats on top of the tears acting as a tear stabilizer and barrier protector of the liquid layer underneath. Eyelid margin pathologies, such as inflammation, infection, blepharitis, Meibomian gland dysfunction leads to significant patient distress. Symptoms of these diseases include itching, burning, crusting, watery eyes and discharge. Damage and loss of proper function of these Meibomian glands leads to specific issues of dry eye disease.

Eye care professionals normally detect when the eyelids are in a diseased state during routine office exams. Eye care professionals commonly treat these problems by employing various modalities including topical or oral antibiotics and steroids and almost always a form of at home daily eyelid margin cleaning. The various known methods for cleaning eyelids fall into several categories: 1. Gentle soap or solution alone. 2. Gentle soap or solution on an abrasive pad. 3. Hand held instrument scrub with abrasive pad in office. 4. Hand held instrument scrub with abrasive pad at home.

Gentle soaps and solutions have been used for years to provide daily home cleaning. Baby shampoo and other soaps, such as Ocusoft, are applied by the patient to their eyelids and rubbed in with their fingers. Other spray-on therapy solutions use chemicals, such as hypochlorous acid, to kill eyelid bacteria. There are known problems with these methods, such as the lack of dexterity of the patient, both children and the elderly to effectively apply the treatment, the physical time of contact of the soap to the lid margin and lashes, and the fact many people out of worry and fear of pain or burning, are known to squeeze their eyes tightly together when touching around their eyes. This will prevent the full effect of the treatment from being administered.

Applying gentle soaps and solutions to an abrasive pad or cloth, such as Ocusoft, premoistened pad or Systane eyelid wipes increases the scrubbing potential but at the same time increases the need to be even more dexterous and cautious to the possibility of scratching the surface of the eyeball with the pad causing irritation or even an abrasion.

Hand-held devices are known to be used for cleaning eye lids by eye care professionals in an office setting. Some known hand-held devices use a rotating abrasive sponge pad to clean the eyelids 12 and 14. One known hand-held device, known as a BlephEx® machine, is disclosed in U.S. Pat. No. 9,039,718 and US Patent Application Publication No. US 2014/0214062. Treatment with such a hand-held device, while effective in the office, is not cost effective since patients must rely on office visits every 3 to 6 months for treatment. Also, patients will have to fall back on other less effective methods and less expensive at-home daily eyelid cleaning.

In order to improve at-home treatment, a hand-held device was developed for use at home to clean the eyelid margins, known as a NuLids™ soft tip device (https:/youtube/6aqOfECykLY). The NuLids device, available from NuSight Medical Operations (https:/www.nusightmedical.com/), includes a hand-held tool with a moving brush. Unfortunately, the NuLids device requires a doctor's prescription and requires disposable pads. Also, treatment with the NuLids device requires significant amount of dexterity to avoid touching the tips to the cornea and requires the user to look in the mirror for proper tip position. This requirement is an obstacle for those needing glasses to see and those with a general fear of touching around ones open eyes especially in children.

Thus, there is a need for an eyelid cleaning device which is simpler to use and cost effective and provides enhanced at home daily eyelid and eye lash cleaning.

SUMMARY OF THE INVENTION

Briefly, the present invention relates to a hand-held device for home use for cleaning eyelids, eye margins and eye lashes. The device includes a housing, for example, a waterproof housing, which forms a handle, and a cleaning head, attached on one end of the housing. In accordance with an important aspect of the invention, a vibration generator is used to sonically drive the cleaning head. The sonically driven cleaning head provides improved cleaning power relative to known rotating brush devices. In use, the sonically driven cleaning head is placed in contact with one or both eye lids for each eye and either held in a stationary position or moved from side to side or back and forth. The vibration of the cleaning head in contact effectively scrubs the upper eyelid or lower eyelid without the need for vigorous scrubbing or significant agility.

DESCRIPTION OF THE DRAWING

These and other advantages of the present invention will be readily understood with reference to the following specification and attached drawing wherein.

DETAILED DESCRIPTION

Figure 1:
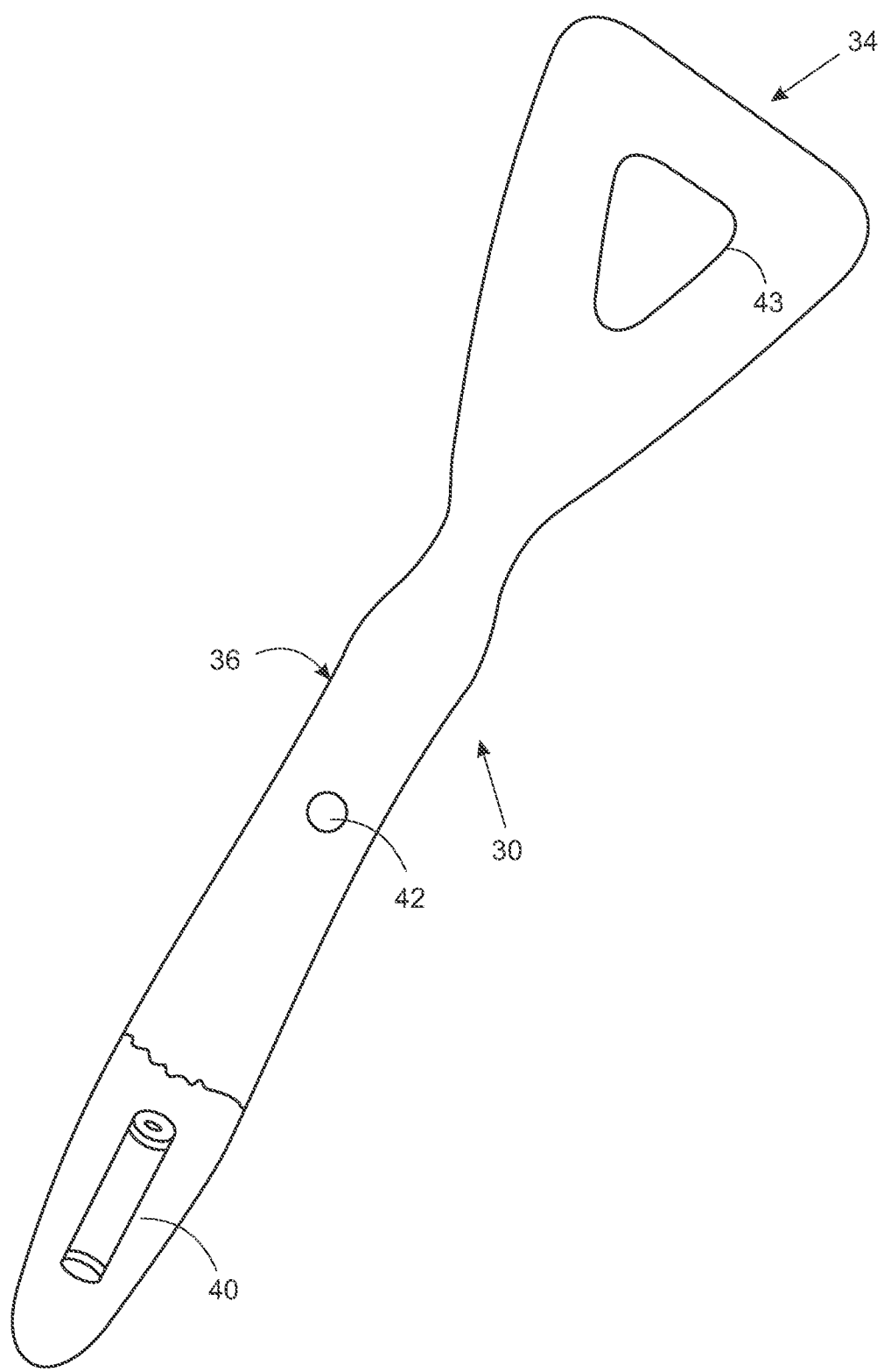
FIG. 1 is a front view of a hand-held device, shown partially broken away, in accordance with the present invention device.
Figure 2:
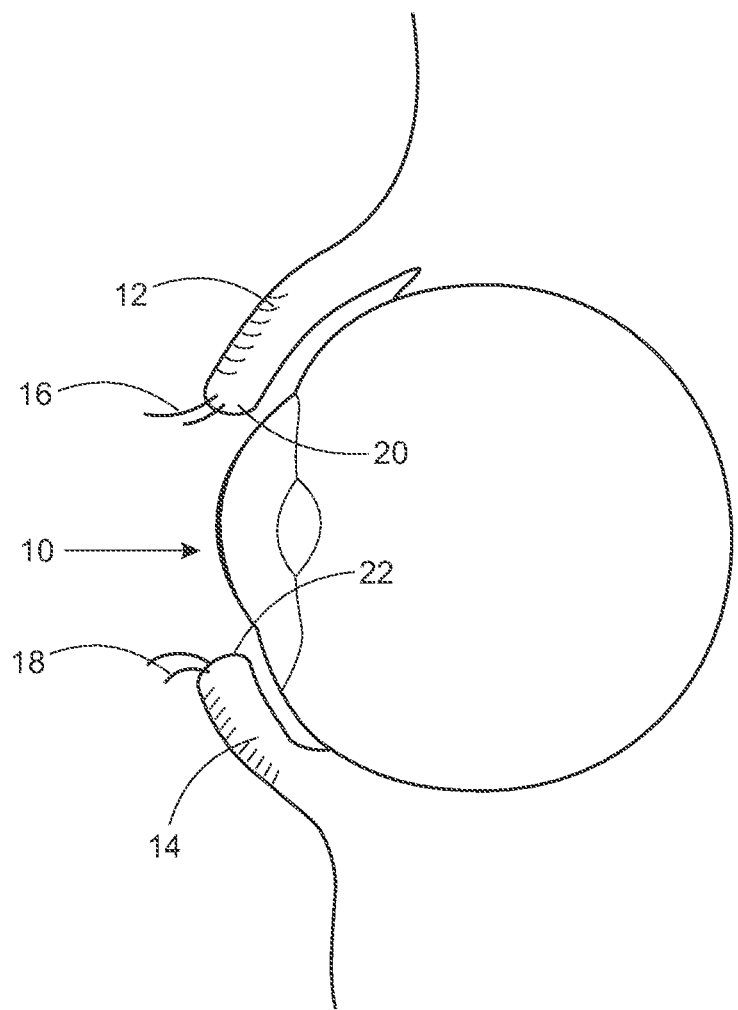
FIG. 2 is a profile view of a human eye illustrating the upper and lower eyelids and eyelashes along the lid margins.

The present invention relates to a hand-held device for home use, generally identified with the reference numeral 30, for cleaning eyelids, eye margins and eye lashes. The device 30 includes a housing, for example, a waterproof housing, which forms a handle, and a cleaning head, attached on one end of the housing. In accordance with an important aspect of the invention, a vibration generator is used to drive the cleaning head sonically. The sonically driven cleaning head is placed in contact with one or both eye lids for each eye and either held in a stationary position or moved from side to side or back and forth. The vibration of the cleaning head in contact effectively scrubs the upper eyelid or lower eyelid, eyelid margins and eye lashes without the need for vigorous scrubbing or significant agility. The vibrating cleaning head is a more effective daily home cleaning tool for eyelids, eye margins and eyelashes than known devices with rotary swabs or sponges.

The device 30 includes a housing 36, for example, a waterproof housing, which forms a handle, and a cleaning head 34 attached on one end of the housing. The handle may be ergonomically formed for patients with dexterity issues and children. The cleaning head 34 may be rigidly attached or removably attached to one end of the housing 36. A power source 38 and a vibration generator 40 are carried by the housing 36. The device 30 may include conventional circuitry to allow the speed and/or amplitude of the vibrations generated by the vibration generator 40 to be varied from sonic to ultrasonic speeds by way of a switch 42, located on the exterior of the housing 36.

Figure 3:
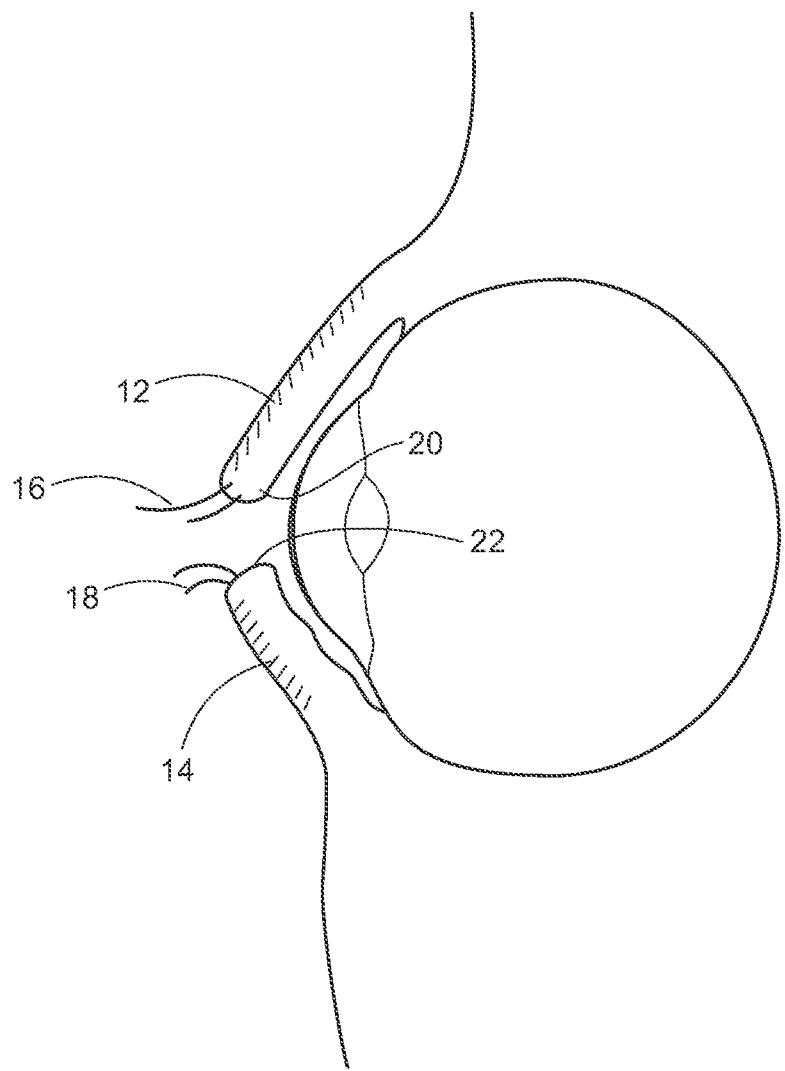
FIG. 3 is similar to FIG. 2 but shown partially closed.
Figure 4:
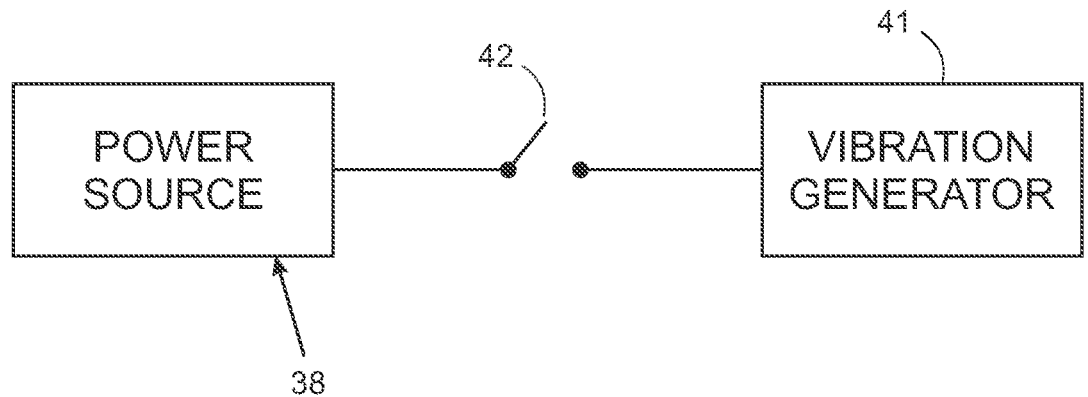
FIG. 4 is a block diagram of vibration system that causes the cleaning head to vibrate.

In use, the eyelids 12 and 14 of one eye are gently closed, for example, as illustrated in FIG. 3. The device allows the upper 12 and lower 14 eyelids and the eyelashes 16 and 18 to be treated by the device 30 at the same time. The head 34 may be formed with a shallow well 43 adjacent a free end of the cleaning head 34. The well 43 is for carrying soap. To clean the eyelids 12 and 14, a gentle soap may be disposed in the shallow well 43 and held in a stationary position in contact with the upper and lower eyelids 12 and 14 of one eye and/or gently moved from side to side and/or up and down to change the vibrational contact with different areas of the eye lids.

The head 34 of the device 30 may be formed with various shapes and contours to enable the comfort and individual cleaning for each area of each eyelid. For example, the shape of the head 34 may conform to the eyelids 12 and 14 when closed. In addition, an elevated ridge may be formed in the cleaning head 43 to align with the juncture of the two closed eyelids, thus increasing the vibrational cleaning at the lid margins 20 and 22 and eyelashes 16 and 18.

The cleaning head 34 may be formed from medical grade silicone, PVC, or other materials that are nonporous, bacteria resistant and hypoallergenic materials that are compatible with a human eye and eyelids. Different types of sanitizing regimens for the cleaning head 34 are suitable for use with the cleaning head 41 are contemplated. For example, the cleaning head 34 may be dipped in a sanitizing solution, such as hydrogen peroxide, after each eyelid is cleaned. Alternatively, sterile protective covers (not shown) can be used and placed over the cleaning head 34 after each use.

There are various advantages of the tool 30 relative to known devices for treating eye lids. The sonically vibrating cleaning head 34 provides relatively more effective cleaning of the eye lids, eye margins and eyelashes than other methods which utilize a rotating brush. Specifically, sonic vibrations are more efficient at removing debris on the eyelids that conventional methods and can be used on all skin types. The sonic cleansing technology disclosed herein uses thousands of pulsations per minute for deep eyelid cleansing. The vibrational energy breaks up crusts and deposits on the eyelids and eye margin. It also creates micro shock waves that can disrupt bacterial cell walls and creates turbulence within the soap to disrupt biofilms by creating pressure waves that creates shear forces and creates micro bubbles that forcefully propel against the tissues to dislodge debris/bacteria.

In addition, the tool 30 requires little manual dexterity which makes it suitable by children and the elderly with dexterity issues. It also allows for the eye to be gently closed during treatment which is more comforting to persons not having to look at an object coming toward their eye. Also, having both eyelids treated at the same time increases compliance and decreases treatment time.

Optionally, each eyelid 12 and 14 may be treated separately. First, a gentle soap is applied to the upper eyelid 12 of one eye. In order to clean the upper eyelid 12, it is partially closed, as shown in FIG. 3. The upper eyelid margin 20 is gently rolled back by one finger. The cleaning head 34 is placed on the exposed upper eyelid margin 20 and upper eyelashes 16 and cleaned by the vibrating action of the cleaning head 34. The soap may be removed from the upper eye lid 12 and eyelashes 16 with a gentle cloth and the cleaning head 34 is then sanitized or replaced before cleaning the lower eyelid 14. Next, A gentle soap is applied to the lower eyelid 14. The lower eyelid 14 is pulled down with one finger to expose the lower eyelid margin 22. The cleaning head 34 is placed on the exposed lower eyelid margin 22 and lower eyelashes 18 and cleaned by the vibrating action of the cleaning head 34. The process is repeated for the other eye. In one embodiment, there are no scrubbing pads or renewables to purchase for daily disposable use, the cost of treatment is greatly minimized.

The device 30 includes a power source 38, for example, one or more rechargeable batteries, such as, lithium batteries or non-rechargeable batteries. The batteries 40 may be located in a removable bottom portion of the housing 36 which allows the batteries 40 to be removed and replaced or recharged. The device may also be configured to be charged by way of a USB port accessible from outside the housing 36. The power source 38 may also be configured to be plugged in to a conventional 120-volt ac receptacle by way of an external power cord (not shown). In such an embodiment, a conventional circuit for converting the 120-volt ac to a DC voltage suitable for operating the vibration generator 40.

Various embodiments of the switch 42 are contemplated. In one embodiment, the vibration generator 41 and the switch 42 may be configured with two modes of operation: an OFF mode and a CLEANING mode. In such a configuration, the switch 42 is used to connect the power source 38 to the vibration generator 41 in a CLEANING mode of operation when the switch 42 is turned to an ON position causing the cleaning head 34 to vibrate. When the switch 42 is in an OFF position, the cleaning head is stationary.

As mentioned above, the device 30 includes a vibration generator 41 that is attached to the cleaning head 34 in order to cause the cleaning head 34 to vibrate when the vibration generator 41 is turned ON. Vibration generators for hand held devices are known in the art. For example, U.S. Pat.

Nos. 8,272,091 and 5,138,733, as well as US Published Patent Application Nos. US 2016/0206412; US 2015/0327964; and US 2009/0226241, all hereby incorporated by reference, disclose a suitable vibration generator for use as the vibration generator 41. The vibration generator 41, power source 38 and the switch 42 are all electrically coupled together.

Obviously, many modifications and variations of the present invention are possible considering the above teachings. Thus, it is to be understood that within the scope of the appended claims, the invention may be practiced otherwise than as specifically described above.

I claim:

1. A device for cleaning human eyelids and eyelashes, the device comprising:
   a housing;
   a power source;
   a vibration generator responsive to said power source for generating sonic vibrations;
   a switch defining an OFF mode and a CLEANING mode-for-selectively connecting said vibration generator to said power source in a CLEANING mode to cause said vibration generator to generate sonic vibrations and an OFF mode for selectively disconnecting said power source from said vibration generator, said switch and said vibration generator being carried by said housing; and
   a cleaning head attached to one end of said housing which causes said cleaning head to be driven by sonic vibrations when said vibration generator is in a CLEANING mode, wherein said cleaning head is configured to conform to the upper and lower eyelids when closed to treat upper and lower eyelids and eyelashes at one time.

2. The device as recited in claim 1, wherein said cleaning head is formed as an irregularly shaped block.

3. The device as recited in claim 1, wherein said cleaning head is formed from a material compatible with a human eye and eyelids.

4. The device as recited in claim 1, wherein said cleaning head is further configured with a shallow well for carrying soap.

5. The device as recited in claim 1, wherein said cleaning head is formed from a non-porous material.

6. The device as recited in claim 5 wherein said cleaning head is formed from PVC.

7. A device for cleaning human eyelids and eyelashes, the device comprising:
   a housing;
   a power source;
   a vibration generator responsive to said power source for generating sonic vibrations;
   a switch defining an OFF mode and a CLEANING mode-for-selectively connecting said vibration generator to said power source in a CLEANING mode to cause said vibration generator to generate sonic vibrations and an OFF mode for selectively disconnecting said power source from said vibration generator, said switch and said vibration generator being carried by said housing; and
   a cleaning head attached to one end of said housing which causes said cleaning head to be driven by sonic vibrations when said vibration generator is in a CLEANING mode, wherein said cleaning head is configured to conform to the upper and lower eyelids when closed to treat upper and lower eyelids and eyelashes at one time, wherein said power source, and wherein said power source is configured to be powered by an external 120-volt ac supply.

8. A device for cleaning human eyelids and eyelashes, the device comprising:
   a housing;
   a power source;
   a vibration generator responsive to said power source for generating sonic vibrations;
   a switch defining an OFF mode and a CLEANING mode for connecting said vibration generator to said power source in a CLEANING mode to cause said vibration generator to generate sonic vibrations and an OFF mode for selectively disconnecting said power source from said vibration generator, said switch and said vibration generator being carried by said housing; and
   a cleaning head attached to one end of said housing which causes said cleaning head to be driven by sonic vibrations when said vibration generator is in a CLEANING mode, wherein said cleaning head is configured to conform to the upper and lower eyelids when closed to treat upper and lower eyelids and eyelashes at one time, wherein said power source includes one or more batteries.

9. The device as recited in claim 8, wherein said one or more batteries are located adjacent a bottom end of said housing.

10. The device as recited in claim 8, wherein said housing is configured to enable the said one or more batteries to be removed from said housing for replacement.

11. The device as recited in claim 8, wherein said housing includes charging contacts to enable the said one or more batteries to be charged from outside of the said housing.

12. A device for cleaning human eyelids and eyelashes, the device comprising:
   a housing;
   a power source;
   a vibration generator responsive to said power source for generating sonic vibrations;
   a switch defining an OFF mode and a CLEANING mode-for-selectively connecting said vibration generator to said power source in a CLEANING mode to cause said vibration generator to generate sonic vibrations and an OFF mode for selectively disconnecting said power source from said vibration generator, said switch and said vibration generator being carried by said housing; and
   a cleaning head attached to one end of said housing which causes said cleaning head to be driven by sonic vibrations when said vibration generator is in a CLEANING mode, wherein said cleaning head is configured to conform to the upper and lower eyelids when closed to treat upper and lower eyelids and eyelashes at one time, wherein said power source is configured to enable the speed of said vibrations to be varied.

13. The device as recited in claim 12, further including a switch mounted on the exterior of said housing that enables said speed of vibrations to be selectively varied.

14. The device as recited in claim 12, wherein said power supply is configured to enable the speed of said vibrations to be selectively varied from sonic to ultrasonic speeds.

15. A device for cleaning human eyelids and eyelashes, the device comprising:
   a housing;
   a power source;
   a vibration generator responsive to said power source for generating sonic vibrations;

a switch defining an OFF mode and a CLEANING mode-for-selectively connecting said vibration generator to said power source in a CLEANING mode to cause said vibration generator to generate sonic vibrations and an OFF mode for selectively disconnecting said power source from said vibration generator, said switch and said vibration generator being carried by said housing; and a cleaning head attached to one end of said housing which causes said cleaning head to be driven by sonic vibrations when said vibration generator is in a CLEANING mode, wherein said cleaning head is configured to conform to the upper and lower eyelids when closed to treat upper and lower eyelids and eyelashes at one time, wherein said power supply is configured to enable the amplitude of said vibrations to be varied.

16. The device as recited in claim 15, further including a switch mounted on the exterior of said housing that enables said amplitude of vibrations to be selectively varied.

* * * * *